(12) United States Patent
Esser et al.

(10) Patent No.: US 6,880,385 B2
(45) Date of Patent: Apr. 19, 2005

(54) METHOD AND APPARATUS FOR PERFORMING DYNAMIC MECHANICAL ANALYSES

(75) Inventors: Ulrich Esser, Gossau (CH); Thomas Hütter, Niederrohrdorf (CH)

(73) Assignee: Mettler-Toledo GmbH, Greifensee (CH)

(*) Notice: Subject to any disclaimer, the term of this patent is extended or adjusted under 35 U.S.C. 154(b) by 0 days.

(21) Appl. No.: 10/405,824

(22) Filed: Apr. 2, 2003

(65) Prior Publication Data

US 2003/0188585 A1 Oct. 9, 2003

(30) Foreign Application Priority Data

Apr. 3, 2002 (DE) .......................................... 102 14 756

(51) Int. Cl.⁷ ................................................. G01N 3/08
(52) U.S. Cl. ..................................................... 73/82.6
(58) Field of Search .................... 73/826, 772, 789, 73/808, 830, 856; 473/56

(56) References Cited

U.S. PATENT DOCUMENTS

| | | | |
|---|---|---|---|
| 3,969,930 A | * 7/1976 | Prevorsek et al. | ............. 73/772 |
| 4,466,292 A | * 8/1984 | Milazzo | ........................ 73/789 |
| 5,287,749 A | * 2/1994 | Nakamura | ..................... 73/808 |
| 5,641,058 A | * 6/1997 | Merten et al. | ......... 198/810.04 |
| 6,058,784 A | * 5/2000 | Carroll et al. | ................. 73/856 |
| 6,098,465 A | 8/2000 | Matsumoto et al. | |

FOREIGN PATENT DOCUMENTS

| | | |
|---|---|---|
| DE | 222120 | 5/1985 |
| DE | 4229549 | 3/1994 |
| EP | 0921388 | 6/1999 |

OTHER PUBLICATIONS

Gerhardt, Joachim, Amplituden–Und Null– Lageregelung für Sinusförmige . . . , in: TM–Technishes Messen 67, 2000, 6, S. 274–282.

* cited by examiner

*Primary Examiner*—Edward Lefkowitz
*Assistant Examiner*—Octavia Davis
(74) *Attorney, Agent, or Firm*—Friedrich Kueffner

(57) ABSTRACT

In a dynamic mechanical analysis, a test specimen is coupled to an excitation device by a holder device. An excitation force made up of a static pre-tensioning force component and a time-variable force component is applied to the test specimen, and a deformation of the test specimen is measured by one or more displacement sensors. In a test phase an excitation force is applied to the test specimen, while at least one decision parameter is determined. The decision parameter is indicative of a degree of slack in the coupling of the test specimen. Based on the comparison between the decision parameter and at least one reference value it is determined whether or not the test specimen is coupled to the excitation device in a completely slack-free state, so that any measured physical values will not be subjected to errors caused by an insufficient amount of the pre-tensioning force.

18 Claims, 6 Drawing Sheets

METHOD AND APPARATUS FOR PERFORMING DYNAMIC MECHANICAL ANALYSES

BACKGROUND OF THE INVENTION

The invention relates to a method of performing dynamic mechanical analyses, wherein a specimen under investigation is held in a holder device and is subjected to a static pre-tensioning force and a time-variable excitation force generated by an excitation device, and wherein the deformation of the specimen is measured by means of one or more displacement sensors. The invention further relates to an apparatus for performing the method. Included in the apparatus are a controller device that directs and controls the analysis process, a holder device for holding the specimen, an excitation device that allows a static pre-tensioning force and a time-variable excitation force to be applied to the specimen, and one or more displacement sensors to measure the deformation of the specimen.

Dynamic mechanical analyses (DMA) are used to determine visco-elastic material properties. To perform a dynamic mechanical analysis, the samples to be investigated are clamped in specimen holders or, in more general terms, connected to suitable holder devices, and stressed with a dynamic force. In order to determine physical quantities from the DMA test, a time profile is registered of the displacement of the specimen and the excitation force acting on the specimen. Of particular interest among the data collected for the excitation force and the displacement are the ratio between excitation force and displacement as well as the phase lag between the two variables. Taking into account the specimen dimensions and the specifics of the excitation arrangement, this information can be used to determine the components of the complex stress/strain tensor or, in other words, to determine an elastic component and a viscous component of the modulus of elasticity. The dynamic mechanical analysis characterizes the visco-elastic behavior, for example under the influence of temperature, different excitation frequencies, phase changes, or chemical transformation of the specimen. To perform temperature-dependent measurements, the specimen is arranged in a test compartment in which the temperature can be varied.

Methods and apparatus for dynamic mechanical analyses are known, e.g., from U.S. Pat. Nos. 5,710,426, 6,058,784, EP 0078373A1, EP 1126269A1, DE 4229549A1, DD 222120A1, U.S. Pat. No. 6,098,465 and EP 0921388A2. The state-of-the-art systems include at least a specimen holder or holder device for a test specimen, an excitation device, and a displacement sensor. The excitation device is connected to an excitation part of the holder device. An anchoring side of the holder device is connected to a stationary part of the measuring apparatus. The excitation force acting on the test specimen can be determined, e.g., by a measurement with a force sensor, or from the voltage and/or current supplied to the excitation device. As a result of the excitation force, the specimen exhibits a deformation that is measured by the displacement sensor, which is arranged at the excitation side of the holder device.

In situations where test samples are subjected to both a base load (i.e., a static force) and a dynamic force, the results have errors if an inadequate base load is selected. For example, a tensile test specimen in an experiment to investigate a correlation between a tensile force and an elongation can be clamped in place with a slack so that, as a result, the dynamic force will not provide an effective elasticity measurement of the test specimen because at least a part of the dynamic force is used to put the specimen completely under tension. The clamping of the test specimen has an analogous effect on the measurement in the case of compressive or bending test samples. The amount of pre-tension required for the desired type of coupling of the test specimen to the excitation device can change during a measurement process, for example if the dimensions of a specimen change because of a temperature change.

If in a dynamic mechanical analysis of a polymer the temperature is raised towards the glass transition temperature of the polymer, it is possible for the polymer material to soften by a factor 1000. When the measurements approach the glass transition temperature, an amount of pre-tension that was required at low temperatures will produce such a strong deformation of the specimen that the measurements can be made only within a limited temperature range. Thus, it is impossible in a range of particular interest, i.e., in a critical temperature range approaching the glass transition temperature, to perform continuous measurements if the same amount of pre-tension is used that is required at a low temperature. In addition to the problems that occur with samples that become softer or expand as a result of a temperature change, there are also measurement problems associated with test samples that shrink under a temperature change.

In the known state of the art of dynamic mechanical analysis devices, the amount of pre-tension used may in some cases be too small, or it may be unnecessarily large. No efficient way is known for monitoring the pre-tension in the sense of ensuring that the test specimen is fully pre-tensioned or, in other words, coupled correctly (i.e., without slack) to the excitation device. The errors introduced into the measurement by an insufficient amount of pretension remain unaccounted for or are ignored. Because the physical measurement values that apply to a correctly coupled specimen can be different at a higher amount of pre-tension, the measurement can also be impaired by an excessive amount of pre-tension.

OBJECT OF THE INVENTION

It is therefore the objective of the present invention to propose a method and an apparatus that keep a dynamic mechanical analysis free of the kinds of errors that are introduced by incorrectly selected levels of pre-tension.

SUMMARY OF THE INVENTION

In a dynamic-mechanical analysis method according to the invention, a test specimen is held in a holder device and subjected to a static pre-tensioning force and a time-variable excitation force, and the deformation of the specimen is measured by one or more displacement sensors. The method includes the steps that during application of a variable excitation force one or more decision parameters are determined and compared to one or more given reference values, and that the comparison is used to determine whether or not the test specimen is completely coupled to the excitation device, i.e., in a completely slack-free state, so that the physical values derived from the measurements will not be subject to errors caused by insufficient amounts of pre-tension.

A dynamic-mechanical analysis apparatus according to the invention includes a control device that directs and controls the analysis process, a holder device to hold the test specimen, an excitation device to apply a static pre-tensioning force and a time-variable excitation force to the test specimen, and at least one displacement sensor to measure the deformation of the test specimen. The control device includes means whereby during application of a variable excitation force one or more decision parameters are determined and compared to one or more given reference values. The result of the comparison is presented in a form that makes it evident whether or not the test specimen is completely coupled to the excitation device so that the physical values derived from the measurements will not have errors caused by insufficient amounts of pre-tension.

The present invention is based on the premise that the excitation force is composed of a substantially constant component and a time-variable component, for example with a sinusoidal variation. The constant portion may be referred to as pre-tensioning force. If the pre-tension is less than a minimally required pre-tensioning force, the specimen is not coupled correctly to the excitation device. In this condition, even a small increase of the force can cause a relatively large amount of displacement, but because of the faulty clamping of the test specimen the displacement does not represent an effective tensile elongation of the entire specimen. For example, if the test specimen is a flat strip of material and is clamped in a slightly misaligned position with a small amount of pre-tension in a holder device for tensile tests, the measurement will account for the visco-elastic properties of only the taut portion of the strip. In the rest of the specimen strip, the variable force component will only cause an increase and decrease in the amount of slack. An amount of visco-elasticity or a spring constant of the specimen measured with an insufficient level of pre-tension is therefore smaller than the effective spring constant of he specimen. As the pre-tension or constant force component of the excitation device is raised, one finds a transitional range for the modulus of elasticity or the spring constant. Above the transitional range, a larger value is measured for the modulus of elasticity than with a pre-tension that is below or within the transitional range. As the pre-tension is increased through the transitional range, the spring constant increases from a lower value that was falsified by an insufficient amount of pre-tension to the higher, correct value. Put another way, the ratio of the dynamic force change to the associated change in displacement cannot be used for determining the spring constant unless the pre-tension is above the transitional range. Analogously, a damping constant of an elastic specimen can only be determined at a sufficiently large pre-tensioning force. If the dynamic excursion of the force acting on the test specimen runs partially into the transitional range, a part of the force will be used to pull the specimen into a taut, flat condition. In an extreme case where no force at all is transferred through the specimen between the excitation part and the anchoring part of the holder device, the effect of the dynamic force may be reduced to accelerate a mass or in some cases to put work into so-called parasitary springs, i.e., deformable elements other than the test specimen. A time graph of the specimen displacement and/or the effective force acting on the specimen will in such a case not have mirror-symmetrically shaped maxima and minima even though the excitation current to generate the force oscillates symmetrically relative to its mean value.

In order ensure correct measuring results without applying unnecessarily large forces to the test specimen, the static force component should be minimal and the total force, i.e., the sum of the static and dynamic components should essentially always be above the transitional range. A method and/or apparatus according to the invention provides at least one decision parameter that is dependent on the static pre-tensioning force and on the amplitude of the dynamic force component and indicates whether the measurement is operating in the transitional range or above the transitional range. By comparing the one or more decision parameters to at least one given reference value, a determination is made as to whether or not the test specimen is completely coupled to the excitation device, so that the physical values derived from the measurements will not be falsified by an insufficient amount of pre-tension.

The determination of a decision parameter can be based, e.g., on points in a force/displacement diagram or values for the visco-elasticity, preferably spring constants, that were found for different amounts of pre-tension. When a transitional range from a first to a second slope is observed in the force/displacement diagram, or if there is a change in the values found for the visco-elasticity or the spring constant, a first value will be assigned to the decision parameter for pre-tensioning forces above the transitional range, or for pre-tensioning forces that are associated with the larger spring constant. A comparison of the first value to a given reference value is used to indicate that the amount of pre-tensioning force is sufficient. To collect the data for the transitional range, one can start for example with a measurement where the pre-tensioning force is set to zero and then continue with a stepwise increase in the pre-tensioning force. It has been found that the determination of a decision parameter through values of a force/displacement diagram or values of the visco-elasticity requires a high volume of calculations. In addition, there has to be a transitional range in order to use the concept of a pre-tensioning force above the transitional range to ensure that the physical values will not have errors due to incorrect coupling of the specimen. If the specimen is correctly coupled to the test apparatus already with a zero amount of pre-tension applied by the excitation device, it will be impossible to find a transitional range, which creates the risk that in the search for a transitional range the test specimen will be stressed by an unnecessarily high pre-tensioning force.

If one or more series of measurements are taken at least over limited segments of time to determine the deformation and, if necessary, also the effective amount of force acting on the specimen, the decision parameter can be defined as a quantity that indicates the degree to which the time series of measurements or curves derived from those measurements are similar to a reference curve shape that would be expected with a complete coupling of the specimen to the test apparatus. If the time-variable excitation force component is generated by a time-variable component of the excitation current that is divided into segments which are symmetric relative to a median line, preferably in the shape of a sine wave, one would expect to also find the data of a series of measurements to show a pattern of symmetric time segments. The at least one decision parameter can be designed to serve as an indicator for an asymmetry between the curve shapes around adjacent minima and maxima of the measurement series. An asymmetry in the measurement data relative to a median level of the displacement or force is indicative that the test variables are at least partially in the transitional range. If this kind of asymmetry is detected, the pre-tensioning force is increased, and/or the dynamic force component may be decreased, in order to bring the test conditions above the transitional range of the pre-tensioning force and into a range where the aforementioned measurement series will result in symmetric curve shapes. At a point where the time-variable force component enters into the transitional range, there will be a break in the data curve. Thus it is also possible to use an analysis method that is directed at finding breaks in the data curves. The analysis of the curve shapes can be performed through methods that require only a low volume of calculations. It is considered self-evident that the respective data series and curve shapes for complete versus incomplete coupling of the specimen to the apparatus can also be measured or derived from the measurements if the time-variable component of the excitation current is asymmetric. In this case, the decision parameter is designed to indicate the degree of similarity between the measured and the expected curve shape.

If the measurement is made with an excitation force entirely below the transitional range, the measurement curves will have unexpectedly large displacement amplitudes and small force amplitudes. If a maximum for the displacement amplitude or a minimum for the force amplitude is known where the specimen can still be expected to be completely coupled to the apparatus, it is possible in the case of a symmetric data curve to use the amplitude as an indicator to determine whether the pre-tensioning force used in the test is above the transitional range. This kind of determination, which is based on a comparison of amplitudes, is needed only if no transition from an asymmetric to a symmetric curve shape occurs in the tested range of pre-tensioning forces.

The behavior of the specimen, in particular the symptoms that occur as a result of imperfect coupling of the specimen, i.e., an insufficient amount of pre-tension, can also be detected from an analysis of the effective magnitude of the excitation current and the control signals for the excitation device. By being coupled into the excitation device and thus representing a load on the latter, the test specimen causes changes in the amplitude and phase of the excitation current. Thus, the time profile of the excitation current can be compared to a curve shape that would be expected with a perfect coupling of the specimen to the holder device. In this case, the decision parameter would be selected as a quantity that is indicative of deviations from the expected curve shape.

If the dynamic component of the excitation force has the form of a sinusoidal oscillation, breaks in a time series of force and/or displacement data will manifest themselves through higher frequency components in the frequency spectrum of a Fourier analysis. Thus, a quantity that is indicative for the presence of higher frequencies can be selected as decision parameter. Suitable choices for decision parameters are, e.g., Fourier coefficients or, in general terms, goodness-of-fit parameters that change their values if there is a break in the curve shape. For example, if a measured time series of displacement data or force data is fitted to a model function with a component at the excitation frequency and at least one higher-frequency component, preferably a harmonic of the excitation frequency, the ratio between the higher-frequency portion and the excitation-frequency portion can be used as a decision parameter. If the decision parameter exceeds a given threshold value, it can be concluded that the time series contains at least one significant higher-frequency component, which indicates a break in a time graph of the data. Of course, the technique of a Fourier analysis can also be applied to detecting an asymmetry between the half-periods of a time graph or time series instead of detecting a break, in order to determine one or more decision parameters that are based on an asymmetry rather than on a break.

The type of excitation used in measurements from which physical data are derived is normally a sinusoidal excitation (see ISO standard 6721-1 1994(E), paragraph 3.1). The standards specify in most cases an excitation at a single frequency. This automatically implies a sinusoidal excitation, because any other periodic curve shape contains harmonics, i.e., more than one frequency. Preferably, the excitation used to determine the one or more decision parameters is an excitation force with the time profile of a sine wave. Because the sine function can be continuously differentiated any number of times, a sinusoidal excitation is considered to be the most benign form of excitation. However, one could also use other forms of excitation to determine the one or more decision parameters, in particular if the task of detecting an insufficient amount of pre-tension could be simplified by a non-sinusoidal excitation.

A decision parameter could also be based on concepts known from the field of signal-propagation theory, for example the harmonic distortion ratio. In some cases it may be practical to merely display a representation of the displacement or force as a function of time over one period of the dynamic excitation. An operator can tell from visual inspection whether the data series is symmetric relative to a median level of the displacement or force. The decision factor used by the operator is in this case a visual impression of the curve shape or more specifically, the degree of similarity between the measured curve and an expected curve shape, in particular the symmetry of the curve. If the data measured over one oscillation cycle appear asymmetric, one has to conclude that a physical value derived from the measurement will have errors. The operator can increase the level of pre-tension until the displayed measurement series appears symmetric, i.e., has half-periods that are substantially mirror images of each other relative to a median line. If the curve shape is symmetric, the risk of errors in the derived physical values because of an insufficient pre-tensioning force can essentially be excluded.

A preferred embodiment of the invention includes a step where following a measurement to determine physical properties of a specimen, the pre-tensioning force is lowered and the one or more decision parameters are evaluated until an asymmetry is found that indicates an insufficient level of pre-tension. At this point, the pre-tensioning force is raised slightly until the asymmetry disappears, so that a sound measurement can be performed for the determination of physical values of the test specimen. This procedure is advantageous in particular for measurements where the temperature approaches the glass transition temperature, because it prevents the pre-tensioning force during the entire measurement series from becoming too high for the progressively softening test specimen and causing an excessive elongation of the latter.

BRIEF DESCRIPTION OF THE DRAWINGS

The following detailed description of a preferred embodiment of the invention refers to the attached drawings, wherein.

DESCRIPTION OF PREFERRED EMBODIMENTS

Figure 1:
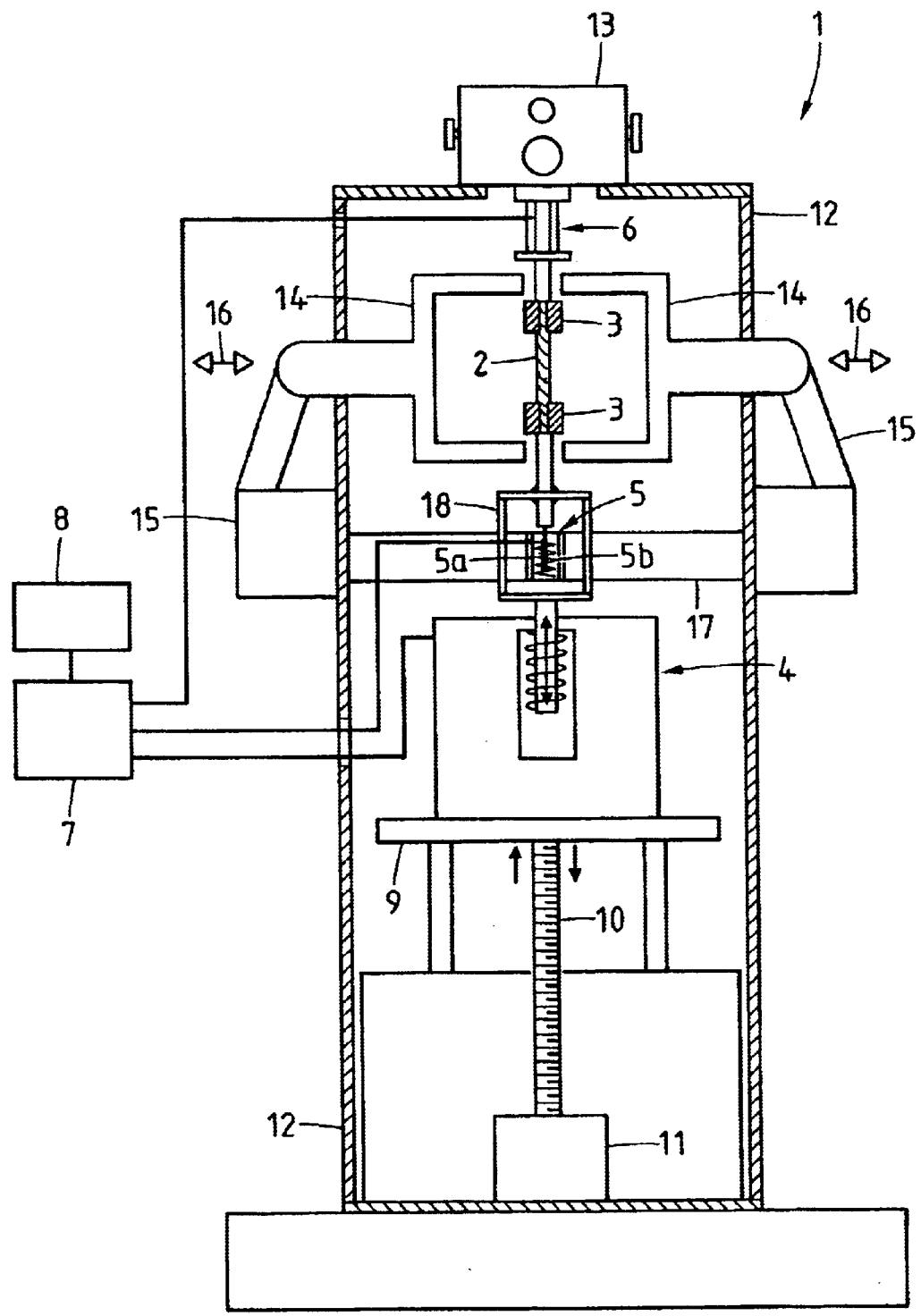
FIG. 1 represents a schematic view of an apparatus for performing dynamic mechanical analyses.

FIG. 1 illustrates an apparatus 1 for performing dynamic mechanical analyses on a test specimen 2. The specimen 2 is held by a holder device 3, and an excitation device 4 applies a static pre-tensioning force and a time-variable excitation force to the specimen. The deformation of the specimen 2 is measured by at least one displacement sensor 5. The apparatus 1 preferably includes a force sensor 6 which can measure the entire force applied to the specimen 2 or may be designed to measure only the dynamic portion of the force. The excitation device 4, the displacement sensor 5, and the force sensor 6 which may be provided in some embodiments of the apparatus are tied to a control- and data-collecting device 7 which is connected to an operating device or input/output device 8. It is considered self-evident that the displacement of the lower end of the specimen could also be transmitted through a transfer mechanism to a displacement sensor mounted in the upper part of the apparatus. This would reduce the possibility of errors due to deformations of the housing or chassis frame of the apparatus. The excitation device 4 is arranged on a height-adjustable stage platform 9 that is preferably equipped with a threaded spindle 10 and a drive source 11 for raising and lowering the stage platform. The apparatus 1 includes a frame 12, and an adjustment device 13 may in some cases be arranged at the top of the frame. The adjustment device 13 connects the holder device 3 or, if applicable, the force sensor 6 to the frame 12. Preferred embodiments of the invention may include an oven 14 that is configured in two parts and connected through a positioning mechanism 15 to the frame 12. With the positioning mechanism 15, the two halves of the oven 14 can be moved towards each other and away from each other as indicated by the arrows 16. The displacement sensor 5 is connected to the frame 12 through a displacement-sensor mount 17. A connector part 18 serves to connect the excitation device 4 to the holder device 3.

Conventional excitation devices 4 are configured as electro-mechanical converters and preferably include at least one permanent magnet and a wire coil arranged in the magnetic field of the permanent magnet. To generate a pre-tensioning force, a direct current of constant magnitude is fed to the wire coil. The dynamic excitation force is produced by superimposing a variable component on the direct current. In addition to the excitation force, the excitation device also provides a guiding constraint wherein the guide function is realized, e.g., through linear-motion guide elements or with elastically flexible constraining links. In the illustrated configuration, the excitation device works like a loudspeaker in which the current flowing through the voice coil interacts with the static magnetic field to generate the force that oscillates the loudspeaker cone. Because the elastic connection between a chassis-fixed part and the movable coil has to be considered a parasitary spring (i.e., an elastic element other than the test specimen being investigated), the force acting on the specimen cannot be determined with sufficient accuracy from the current flowing through the coil, which makes it necessary to use the aforementioned force sensor 6. If the excitation device does not have parasitary springs, i.e., if it uses low-friction linear-motion guide elements, the force sensor 6 may be unnecessary because the excitation force can in this case be determined with sufficient accuracy from the coil current. As an alternative to excitation devices of the foregoing description, it would also be conceivable to us oscillatory actuators that are based on a piezo-electric working principle or even pneumatic systems.

In principle, the force sensor 6 can be based on any kind of force-measuring concept. The apparatus of the illustrated embodiment works with a quartz-based force sensor based on the piezo-electric effect. Likewise conceivable are sensors with strain gauges. The sensor is configured with two flanges and an electrical connection. In addition, there is an electronic circuit to process the electrical signals so that they can be evaluated with an analog/digital converter. Some preamplifier circuit elements may already be integrated in the sensor elements.

The preferred choice for the displacement sensor 5 is an inductive position sensor which works without mechanical contact between the fixed part and the moving part. A ferromagnetic plunger 5a is rigidly tied to the connector part 18 that transfers the force from the excitation device 4 to the test specimen 2. The plunger 5a is movable up and down inside a coil cylinder 5b that is connected to the chassis frame 12. When the plunger 5a changes its relative position within the coil cylinder 5b, there is a commensurate change in the amount of inductive coupling between different coil windings on the coil cylinder. The change in the inductive coupling is used to generate a displacement signal that can be brought into a measurable form by means of an appropriate measuring amplifier. This sensor concept is known as linear variable differential transformer (LVDT). However, the displacement sensor can also be based on some other concept. In particular, there are a number of optical position sensor principles. For example, some commercially available sensors use an interferometric principle.

Figure 2:
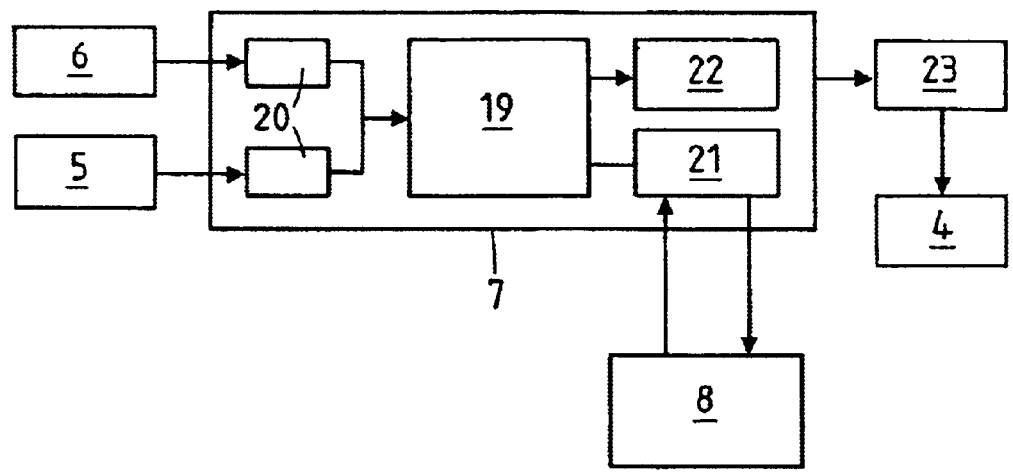
FIG. 2 represents a block diagram of the control and data-collecting arrangement of an apparatus for performing dynamic mechanical analyses.

FIG. 2 shows the control and data-collecting device 7 that is connected to the operating device 8. The latter preferably includes the entire control system of the apparatus, in particular a user terminal, and it may also an interface to other instruments or to computers. The control and data-collecting device 7 includes a controller or processor 19, at least one but preferably two A/D converters 20, an interface 21 and a driver device 22. The interface provides the connection between the controller 19 and the operating device 8 which, in turn, preferably has its own additional controller to direct the process steps required to perform a measurement. Connected to the at least one A/D converter 20 is a displacement sensor 5. If a force sensor 6 is used in addition to the displacement sensor, the force sensor is connected to a second A/D converter. The controller 19 directs the apparatus in the sequence of process steps that are required so that a measurement is performed with a sufficient pre-tensioning force. The controller device supplies the driver device 22 with the appropriate control signals to drive a preamplifier 23 of the excitation device 4, so that the latter is supplied with an excitation current with a constant portion and a variable portion in accordance with the control signals. As a result of the excitation current, the excitation device generates an excitation force with a constant force component and a variable force component. It is considered self-evident that superordinate and parallel process control programs such as, e.g., a temperature regulation program, can likewise run on the controller 19, provided that the latter is designed with the requisite capabilities. The interface 21 would in this case perform the function of an internal interface or a software interface.

Figure 3:
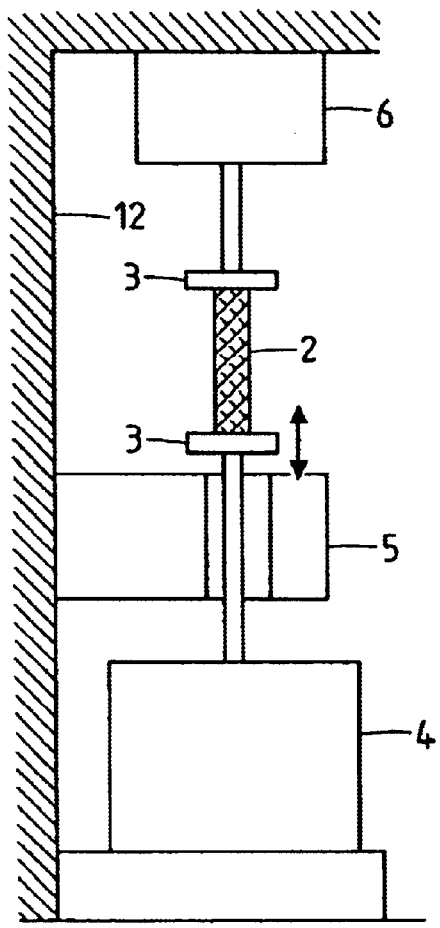
FIG. 3 represents a schematic view of an apparatus for performing dynamic mechanical analyses with a sufficiently pre-tensioned specimen.
Figure 4:
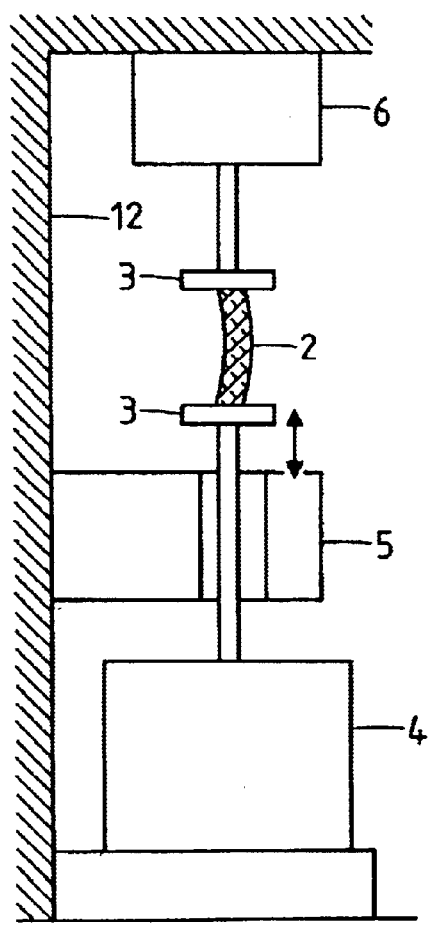
FIG. 4 represents a schematic view of an apparatus for performing dynamic mechanical analyses with an insufficiently pre-tensioned specimen.

FIGS. 3 and 4 illustrate the problem of clamping the test specimen 2 correctly in place, which was discussed herein under "Background of the Invention". The test specimen 2 in FIG. 4 is shown in a bent shape to indicate an insufficient amount of pre-tensioning force. If the specimen 2 is clamped in the holder device with significantly too much slack, the adjustable stage platform 9 (FIG. 1) can be lowered as a first step. Alternatively, the slack could also be removed by generating an appropriate static force with the excitation device. Thus, the stage platform 9, spindle 10 and drive source 11 could also be considered as parts of the excitation device 4, as shown in FIGS. 3 and 4. If the distance between the two parts of the holder device 3 is substantially matched to the free specimen length between the clamps, the sufficient pre-tensioning force is generated as a constant tensile force of the excitation device 4. The constant tensile force needs to be set at a sufficient magnitude that the subsequently measured physical values are free of errors. While FIGS. 3 and 4 illustrate the problem for the case of a tensile test specimen, the detrimental consequences of an insufficient pre-tension on the measuring result are analogous in compression or bending tests. The level of pre-tension required for the desired degree of mechanical coupling of the specimen to the excitation device can change during a measurement process, for example if the dimensions of the specimen change because of a temperature change.

Figure 5:
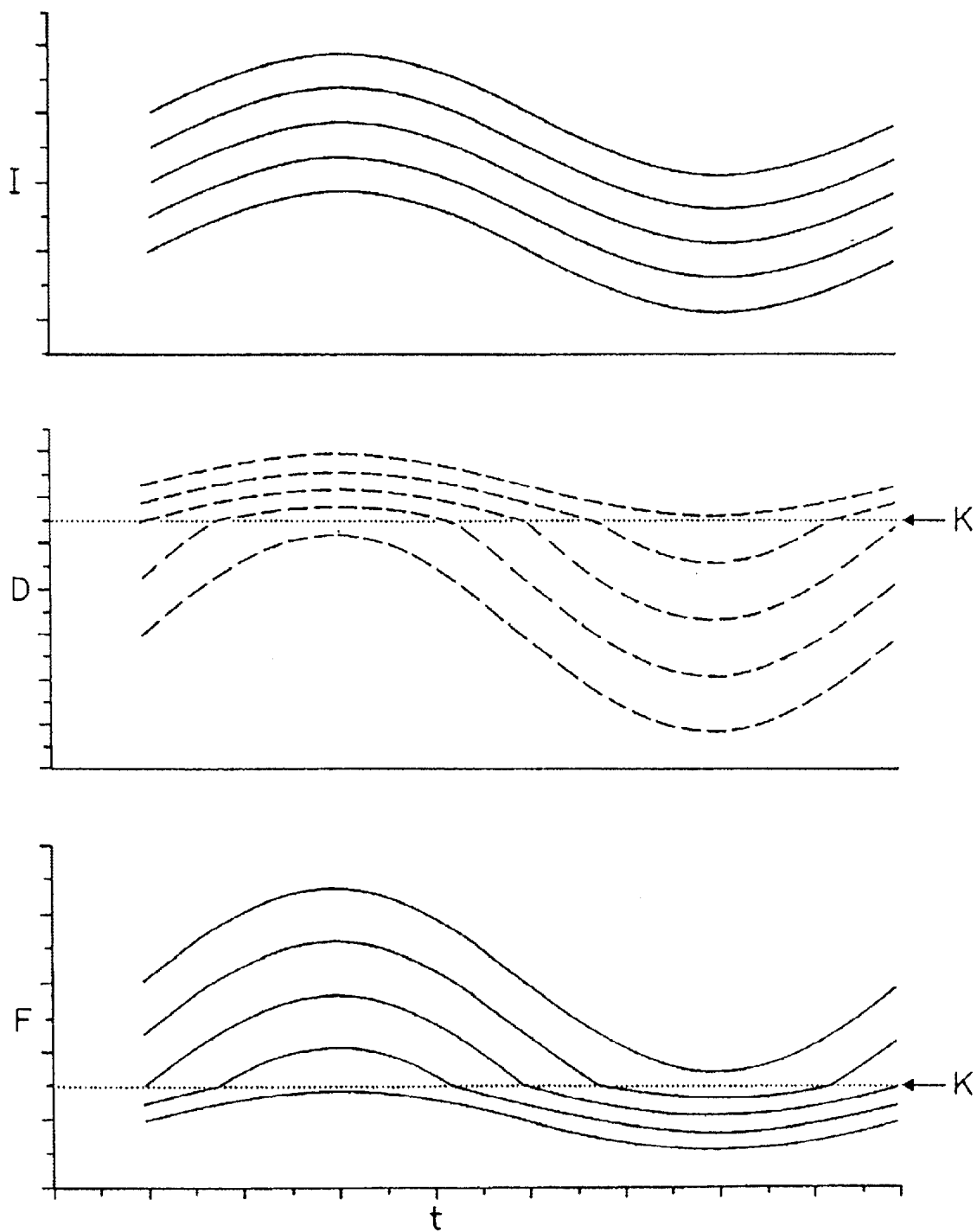
FIG. 5 represents time graphs of the excitation current, displacement, and excitation force for different magnitudes of the pre-tensioning force.

FIG. 5 represents a graph of the excitation current I or of the sinusoidal driver signal for the excitation current as a function of the time t. The different curves running parallel to each other correspond to different amounts of pre-tension. For each curve representing an excitation current, the two other time graphs of FIG. 5 represent, respectively, the associated displacement D and the effective force F acting on the specimen. The curves are based on different series of measurement data taken at different levels of pre-tensioning force. The transitional range discussed above manifests itself in these curves as a break point K in the curve. If the pre-tensioning force is below the break point K, the displacement caused by the force may in an extreme case be determined only by the inertial mass of the measuring system or by parasitary spring forces of guiding constraints. With a complete lack of force-transfer coupling between the holder device and the specimen, the dynamic portion of the effective excitation force will approach zero. This is why the curves below the break point level K of the curves have large amplitudes of the displacement D and small amplitudes of the force F. The opposite is true for the curve segments above the break point level K, where the amplitudes are small in the displacement graph and large in the force graph. In order to prevent the entire measurement from being invalidated by an insufficient pre-tensioning force, the level of pre-tension has to be set high enough that the graphs of the displacement and force are entirely above the break point level K. If the displacement and force are found to be in phase with each other, as is the case in the illustrated example of FIG. 5, this indicates that the specimen 2 is completely elastic and that its spring constant can therefore be determined as the ratio between the minimum-to-maximum differential of the force and the minimum-to-maximum differential of the displacement, or as the quotient of a change in the force divided by the associated change in the displacement. If the determination of the spring constant is based on curves that extend across the break point level or lie below it, one will obtain an erroneous result for the spring constant. Thus, for an error-free measurement, one has to ensure that the data belong to a curve that lies above the break point level K that applies to the current test specimen and the way it is clamped in the apparatus. As will be readily apparent to those familiar with the field of the invention, one could also use measurements of the electrical quantities in the excitation device, i.e., phase and amplitude of excitation current and excitation voltage, to determine properties of the specimen, specifically the integrity of the force-transfer coupling between the specimen and the test apparatus.

All measurement systems have in common that they measure displacements of the test specimen 2. If a measuring apparatus has no parasitary spring effects in the excitation device 4, the data for the excitation force, specifically the force amplitude, can be derived from the power supplied to the excitation device 4, i.e., the alternating current used to drive the excitation, so that the system can in some cases work without a force sensor. The required amount of pre-tensioning force is in this case determined by evaluating the time series of displacement data measured by the displacement sensor. Starting from a low level, the pre-tensioning force is raised until the time series of data lies entirely above the break point level K. In measurement systems that have sensors for the displacement as well as for the force, one can evaluate one or the other or both of the data series for displacement and force in order to set the appropriate amount of pre-tensioning force.

Figure 6:
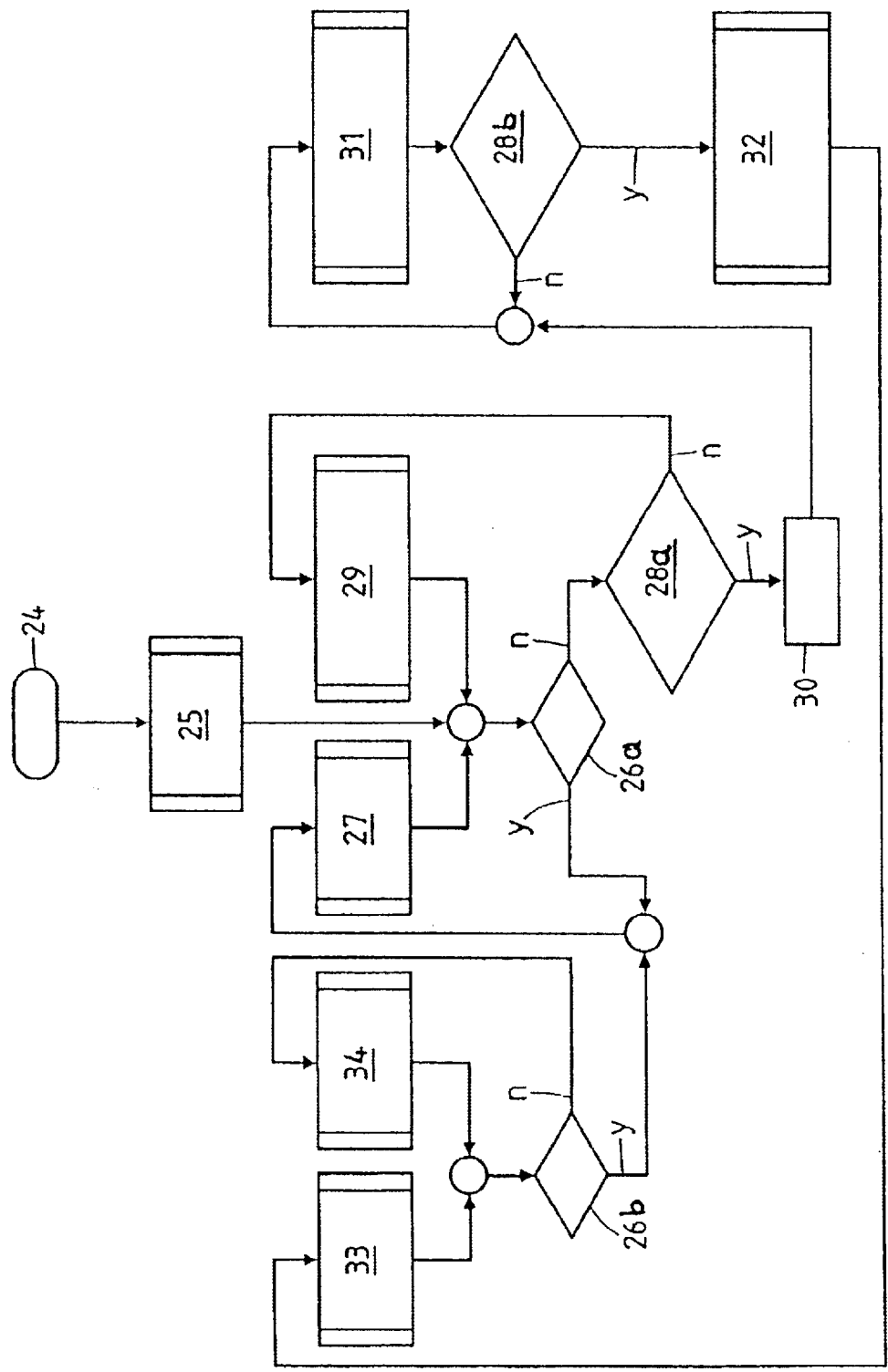
FIG. 6 represents a flow chart of a control process to optimize the pre-tensioning force.

FIG. 6 represents a flowchart for a program to be executed by the controller 19 to optimize the pre-tensioning force. In the illustrated embodiment, the program routine for optimizing the pre-tensioning force is shown without indicating any interdependence with other process control programs performed by the apparatus. It is considered self-evident that the controller program to optimize the pre-tensioning force could also be an integral part of a superordinate process control program that controls additional control variables such as temperature. If the program routine for setting the pre-tensioning force is designed as a separate subroutine for a superordinated main program of the controller, it will be easier to implement the subroutine as a program module in existing analyzer instruments. The subroutine for the pre-tensioning force is started under the control of the main program of the controller device. As a first program step 24, the subroutine is initiated by a starting signal and by an entry of input values such as a force amplitude F, a displacement amplitude x, an additive constant amount p of direct current, and a measuring frequency f.

A first program phase, also referred to herein as test phase, (steps 25 to 30 of the flowchart in FIG. 6) serves to determine the required magnitude of the constant pre-tensioning force or, more specifically, the amount of direct current that produces the pre-tensioning force. A value for the alternating current will be optimized only at a later stage in a second phase of the program. The first program phase is initialized in step 25 by setting a starting level for the direct current, for example zero. The alternating current is set at a low value, and a measurement series is performed at a test frequency $f_{test}$. In this measurement series, a timed sequence of data for the displacement or the excitation force (depending on the configuration of the test apparatus) are taken by means of the at least one A/D converter shown in FIG. 2. In the next following step 26a, the data series is evaluated and a value is assigned to the decision parameter. A yes/no decision is made whether the decision parameter value is in a range that indicates an insufficient pre-tensioning force or an asymmetric time graph of the force and/or displacement. (Note that the steps 26a and 26b perform identical functions at two different stages of the program.) In the affirmative case (y) of step 26a, the program passes to step 27 where the DC level is increased and a new measurement series is performed. The program loops again through the decision step 26a. As soon as the decision parameter value is found to be in a range that indicates a symmetric time graph of the force and/or displacement, i.e., in the negative case (n) of step 26a, the program proceeds to a next decision step 28a. (Note that the steps 28a and 28b perform identical functions at two different stages of the program.)

Step 28a represents a yes/no test whether the oscillation amplitude of the last measured data series is in a range that is consistent with the displacement amplitude x and/or force amplitude F that was set in step 24. In the negative case (n) of step 28a, i.e., if the amplitude of the last measured data series deviates too much from the initially set value, the program proceeds to step 29, where the AC amplitude is increased and a new measurement series is performed. The program proceeds again to the decision step 26a. In the positive case (y) of step 28a, i.e., if the measured amplitude is sufficiently close to the initially set value, the program proceeds to step 30 where the values used for the DC level and the DC amplitude in the last preceding measurement series as well as the measured amplitude are stored in memory. All of the measurement series performed up to this point, i.e., in the test phase of the program, are preferably made with the test frequency $f_{test}$. A value of the test frequency $f_{test}$ is preferably selected under the aspect of obtaining clear test results in the decision steps 26a and 26b, i.e., a clear discrimination between symmetrical and asymmetrical data series. The initially entered frequency f, on the other hand, is to be used for the measurements that are made to determine the actual physical characteristics of the specimen. Of course, the frequencies f and $f_{test}$ may in some cases be the same.

The determination of the physical characteristics of the specimen occurs in a second program phase according to the following description, also referred to as the measurement phase, beginning at step 31 which includes the following operations: The DC level is preferably raised by the small additive constant value p to provide a margin of safety that the measurement series will be symmetric. Another reason to increase the DC level may be to detect a pre-tension dependent behavior of the test specimen. As the spring constant of a test specimen may change with an increase in the pre-tensioning force even in cases where the specimen is fully coupled to the apparatus, the method has to allow measurements to be performed as a function of the pre-tensioning force also for conditions above the transitional range. If necessary, the AC amplitude is adjusted based on the initially entered excitation force amplitude. The excitation frequency is set to the initially selected value f. To test the integrity of the measurement, a decision step 28b (analogous to step 28a) is performed. In the negative case (n) i.e., if the amplitude of the last measured data series deviates too much from the initially set value, the program loops back to step 31. As soon as the step 28b has a positive outcome (y), i.e., if the measured amplitude is sufficiently close to the initially set amplitude, the program proceeds to step 32 where the measurement data required to determine the physical characteristics of the specimen are transmitted through the interface 21 to the operating device 8. The transmitted data include both a displacement amplitude and a force amplitude for the test specimen. In systems that are not equipped with a force sensor, the force amplitude is determined from the amplitude of the AC component of the excitation current. In order to determine the damping coefficient of the spring, it is necessary to also transmit the phase difference between excitation force and displacement. Obviously, the program output could also consist of the entire time series of displacement and excitation data, or the program could directly output the visco-elastic properties of the specimen.

Following step 32, the program proceeds to a third program phase, also referred to as reset phase, starting with step 33. The DC and AC components of the excitation current are reset to the values that were stored in step 30, and a measurement series is performed with the test frequency $f_{test}$. Next, a decision step 26b (analogous to step 26a) is performed. In step 26b the data series is evaluated and a value is assigned to the decision parameter. A yes/no decision is made whether the decision parameter value is in a range that indicates an insufficient pre-tensioning force or an asymmetric time graph of the force and/or displacement. In the affirmative case (y) of step 26b, the program passes to step 27 where the DC level is increased and a new test measurement series is performed. In the negative case (n) of step 26b, i.e., if the decision parameter value is found to be in a range that indicates a symmetric time graph of the force and/or displacement, the program proceeds to step 34. At this point, the program interprets the symmetric time graph as an indication that the pre-tensioning force and, accordingly, the DC component of the excitation current are two large and the DC component is therefore lowered. The rationale for this is to ensure that the pre-tensioning force is reduced if the test specimen is softening, so that the test specimen is not subjected to an excessive load. The procedure according to process step 34 is particularly advantageous if the test specimen changes its length, e.g., under the influence of temperature. However a length change can also occur at a constant temperature, e.g., if a chemical reaction takes place due to exposure of the specimen to a gas atmosphere or to ultraviolet radiation.

The measurements that are performed ahead of the decision steps 26a and 26b, respectively, are preferably made at a fixed frequency $f_{test}$ in a preferred range between 0.1 and 10 Hz. A frequency of less than 0.1 Hz leads to an unacceptably long measuring process cycle. If the frequency is above 10 Hz, it may be impossible to reliably ascertain the symmetry or asymmetry of the measurements. For example, there may be mechanical resonance oscillations interfering with the measurement process. It is in most cases practical to perform the test measurements as well as the re-test meastsurements at one and the same frequency $f_{test}$, in order to ensure identical start conditions even if variable frequency values f are used for the determination of the physical specimen characteristics.

A large frequency range has to be available for the determination of the characteristic physical values of the specimen, for example from 0.001 Hz to 1000 Hz. The entire electro-mechanical system of the apparatus and specimen combined, including the inductivity of the excitation device and the spring constant of the specimen among other factors, has a frequency-dependent behavior. During an actual specimen-analysis measurement, the amplitude at the frequency f is therefore evaluated in the decision step 28b and the AC amplitude of the excitation device is adjusted if necessary. To ensure the versatility of the apparatus for a broad range of applications, the system has the capability to raise the DC component by a selectable amount p for the measurement process in block 31, so that the DC level can be higher than the amount required for achieving symmetric measurement data. With this feature, the dependency of the elasticity on variable levels of pre-tension can be analyzed, which is a characteristic property of polymers.

The visco-elastic property of many materials, polymers in particular, depends to a large extent on the temperature as well as on the excitation frequency. Variations by a factor of 1000 or more are not a rarity. In addition, the visco-elastic properties of a test specimen also depend on the magnitude of an implicit static force, even on the dynamic excitation itself, and often also on the orientation of the test specimen (in anisotropic samples). Taking into account the specimen dimensions, the elastic component and the viscous component of the modulus of elasticity can be calculated from the measured amplitudes and phase difference of force and displacement. To allow an accurate interpretation of the measurement data, it is indispensable to state the test conditions (offset amounts of force and displacement, force amplitude, displacement amplitude, frequency, temperature). It is also desirable to be able to select and preset the values of these parameters within wide ranges.

Figure 7:
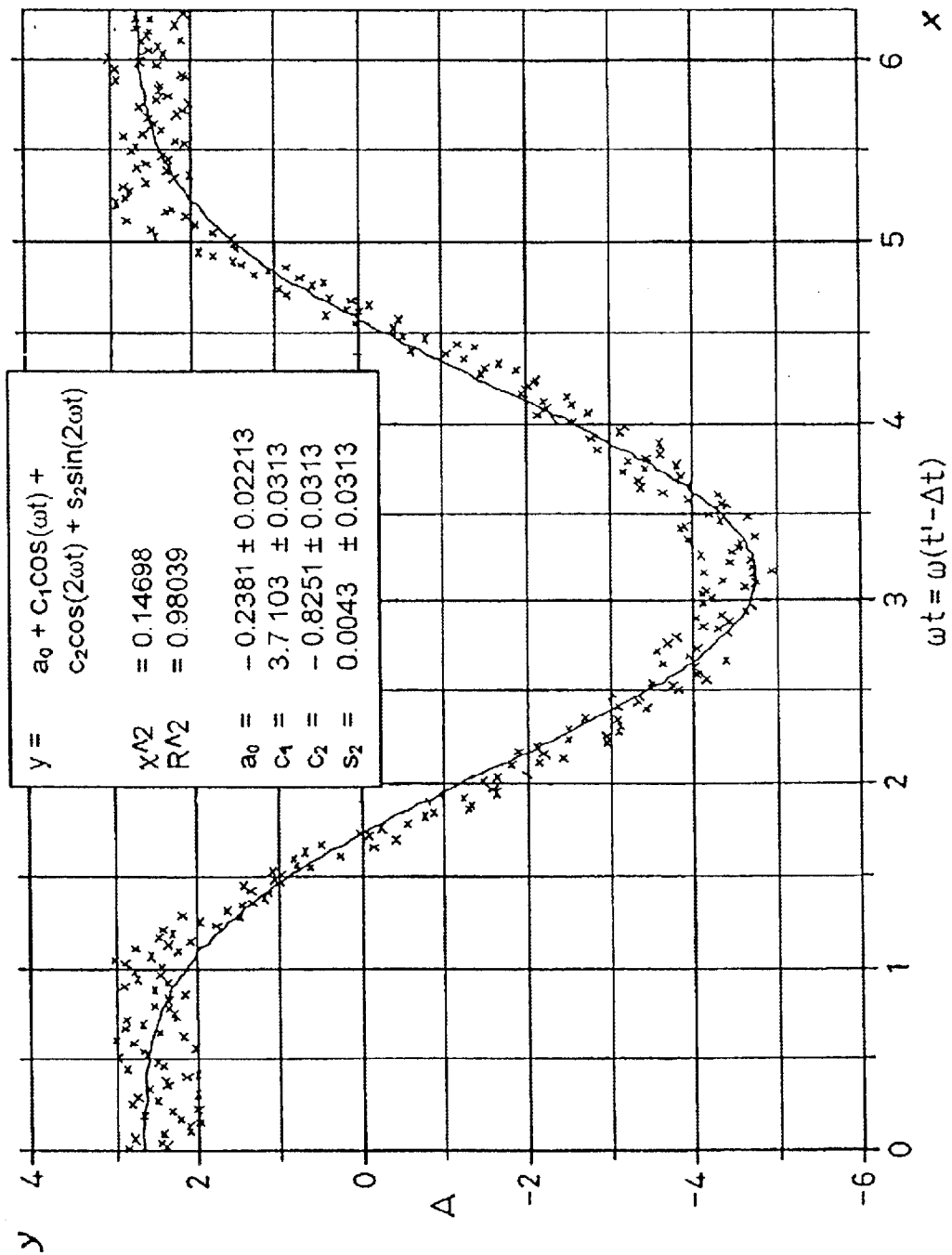
FIG. 7 represents a curve fit between a measured time series of data and a model function.

FIG. 7 illustrates how the decision parameter required in the decision steps 26a, 26b can be based, e.g., on a curve-fitting process of the measured data series to the function $$y = a_0 + c_1 \cos(\omega t) + c_2 \cos(2\omega t) + s_2 \sin(2\omega t).$$

The abscissa in FIG. 7 represents the normalized time axis (oscillation period normalized to 2n), and the ordinate measures the amplitude. The coefficients of the model function are in essence the Fourier coefficients of a Fourier series that has been broken off after the second-order harmonic and time-shifted so that the sine-coefficient of the base frequency disappears. The coefficient $c_2$ for the second-order harmonic describes a signal that is superimposed on the harmonic base frequency signal. A negative coefficient $c_2$ corresponds to a flattening of the positive half-wave and narrowing of the negative half-wave of the data series and thus represents a measure for the asymmetry of the data series. A criterion has to be set as to what represent a significant degree of asymmetry as opposed to a mere random irregularity due to noise. Tests have shown the ratio between $c_2$ and $c_1$ represents a reliable decision parameter and that a significant asymmetry exists if $-c_2/c_1 \geq 0.03$. The values listed in FIG. 7 for $a_0$, $c_1$, $c_2$, $s_2$ are based on fitting the data of a test measurement series to the model function. With the listed values for $c_1$ and $c_2$, the foregoing criterion has the result $-c_2/c_1 = 0.22 \geq 0.03$, which indicates that the data series shown in FIG. 7 is asymmetric.

The test for the symmetry of the data can be further refined by including additional Fourier coefficients in the evaluation process. The coefficients calculated from the curve-fitting process can serve to calculate at least one decision parameter. One could also evaluate the curvature values at the maxima and minima of the data series, i.e., at the points where the curvatures should be equal and opposite for a symmetric signal. This concept leads likewise to an evaluation of Fourier coefficients against appropriately designed criteria.

As a general principle, one can count on the fact that the time graphs of the displacement and force will have a more or less sharp break at the transition from a taut to a slack condition of the specimen and that it will be possible to detect at least the presence of this break in some manner. However, the problem with this assumption is that a relaxation or in general the visco-elastic properties of the test specimen are superimposed on the expected transition effect, so that a break in the graphs will be at least more difficult to detect. In addition, the excitation in the test for finding the pre-tensioning force can be different from the excitation required for the actual measurement of material properties of the specimen, which can likewise have an influence on the shape of the time graphs.

Figure 8:
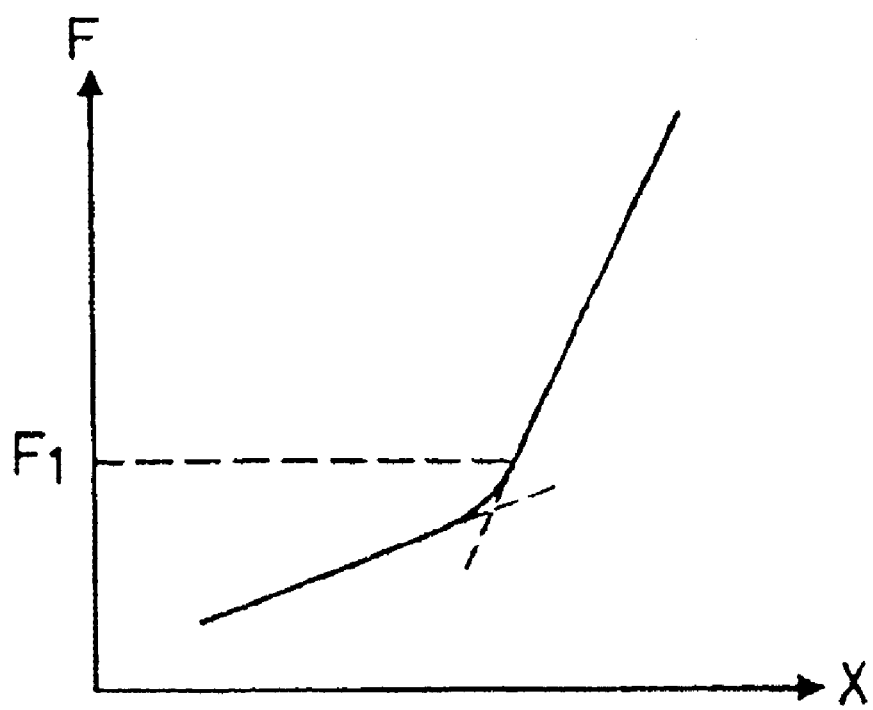
FIG. 8 represents a force/displacement diagram in a transitional range.

FIG. 8 illustrates a force/displacement diagram with a transitional range. If the pre-tensioning force F is less than $F_1$, the measurements made on the test specimen will have errors due to an inadequate coupling of the specimen to the excitation device. As a way of finding a decision parameter, one could for example determine individual points of the force/displacement diagram for different amounts of pre-tensioning force. If a transition can be found from a first slope angle to a second slope angle of the force/displacement diagram, the decision parameter is assigned a value that indicates an adequate pre-tension for points in the diagram that are above the transition ($F > F_1$). In a test measurement to find the transition, one would start, e.g., at the zero level of pre-tensioning force and increase the force in step increments. It has been found that a high volume of calculations is required to determine the decision parameter from points in the force/displacement diagram or from measurements of visco-elasticity. In addition, this technique of determining a sufficient pre-tensioning force only works if a transition range can be found in the time graph. If the sample is completely coupled to the excitation device already without applying a pre-tension through the excitation device, it will be impossible to find a transition range. This creates the risk that the sample may be subjected to an unnecessarily large pre-tensioning force during the search for a transition range.

What is claimed is:

1. A method of performing a dynamic mechanical analysis, wherein a test specimen is coupled to an excitation device by means of a holder device, wherein the excitation device applies an excitation force comprised of a static pre-tensioning force component and a time-variable force component to the test specimen, and wherein a deformation of the test specimen is measured by means of at least one displacement sensor, the method comprising a test phase with the steps:

applying the excitation force to the test specimen;

while said excitation force is in effect, determining at least one decision parameter, said decision parameter being indicative of a degree of slack in said coupling of the test specimen;

comparing said decision parameter to at least one reference value;

based on said comparison, determining whether or not the test specimen is coupled to the excitation device in a completely slack-free state, so that physical values derived from said measurements of the deformation will not be subject to errors caused by an insufficient amount of said pre-tensioning force component.

2. The method of claim 1, wherein determining a decision parameter comprises:

applying different amounts of the pre-tensioning force component;

plotting a force versus displacement diagram for the different amounts of the pre-tensioning force component;

examining whether said diagram contains a transition from a first slope to a second slope; and if the transition is found to be present, assigning to the decision parameter a value which indicates that said pre-tensioning force component is adequate for points in said diagram that are in a range of said second slope.

3. The method of claim 1, wherein said physical values represent a modulus of elasticity of the test specimen and wherein determining a decision parameter comprises:

applying different amounts of the pre-tensioning force component;

determining said modulus of elasticity at said different amounts of the pre-tensioning force component;

examining whether there is a transition from a low modulus of elasticity to a high modulus of elasticity at said different amounts of the pre-tensioning force component; and if the transition is found to be present, assigning to the decision parameter a value which indicates that said pre-tensioning force component is adequate if it is of a magnitude corresponding to said high modulus of elasticity.

4. The method of claim 1, wherein at least one of the deformation and an effective deformation-causing force is represented at least over limited time intervals as a series of data assigned to sequential points in time, wherein said series of data is compared to a reference profile, said reference profile being representative of said completely slack-free state, and wherein said decision parameter is defined so that it allows a quantitative comparison of said series of data to said reference profile.

5. The method of claim 4, wherein the excitation force is produced by means of an excitation current of the excitation device and wherein said effective deformation-causing force is determined from said excitation current, said excitation current comprising a time-variable current component which at least in the absence of said test specimen has a curve profile that is symmetric relative to a median level, wherein the reference profile is represented by said symmetric curve profile and the at least one decision parameter indicates a degree of asymmetric deviation of the series of data from said symmetric curve profile.

6. The method of claim 4, wherein the time-variable force component oscillates with an excitation frequency, wherein said quantitative comparison is performed by approximating the series of data through a model function comprising a base component oscillating symmetrically relative to a median level at said excitation frequency and also comprising a higher-frequency harmonic component, wherein the at least one decision parameter represents a ratio between a second coefficient of the higher-frequency harmonic component and a first coefficient of the base component.

7. The method of claim 4, wherein the at least one decision parameter is determined by performing a Fourier analysis of said series of data.

8. The method of claim 4, wherein the deformation is represented as a first series of data assigned to sequential points in time, and said first series of data is used to determine said decision parameter.

9. The method of claim 4, wherein the effective deformation-causing force is measured by means of a dynamic force sensor, said deformation-causing force is represented as a second series of data assigned to sequential points in time, and said second series of data is used to determine said decision parameter.

10. The method of claim 4, wherein the pre-tensioning force component is produced by means of a direct current and the time-variable force component is produced by means of an alternating current, and wherein said test phase comprises:

a) a starting step (25), wherein starting values are assigned to the direct current and the alternating current and a test measurement series is performed at the starting values and with a test frequency $f_{test}$ of the alternating current, wherein in said test measurement series a test data series is determined for one of the deformation and the excitation force;

b) a decision step (26a), wherein a parameter value is assigned to the decision parameter based on said test measurement series and a yes/no test is made as to whether the parameter value indicates an insufficient amount of pre-tensioning force;

c) in the affirmative case of step b), a DC-adjusting step (27) wherein the direct current is increased, a new test measurement series is performed with the increased direct current, the starting value for the alternating current, and the test frequency $f_{test}$, and the method loops back to step b); and d) in the negative case of step b), a memory-saving step (30) wherein a DC value for the direct current and an AC value for the alternating current are stored in memory.

11. The method of claim 10, wherein a negative outcome of the decision step (26a) is directly followed by an amplitude test (28a) defined as a yes/no test whether the test data series indicates an amplitude of the excitation force conforming to a given range of amplitudes, wherein in the negative case of the amplitude test (28a) the program proceeds to an AC-increasing step (29) and then loops back to the decision step (26a), and wherein in the affirmative case of the amplitude test (28a), the program proceeds to step d).

12. The method of claim 10, wherein the test phase is followed by a measuring phase in which physical values of the test specimen are determined, and wherein said measuring phase comprises:

e) in a measuring procedure (31), adjusting the DC value by an additive amount p, adjusting the AC value if necessary, setting a given measuring frequency f for the alternating current, driving the excitation device (4) with an excitation current in accordance with the DC- and AC values and the frequency f, and performing a measurement series resulting in a series of measurement data;

f) in a data-transmitting step (32), transmitting the measurement data and experimental parameters including DC value, AC value and measuring frequency f to a program that computes said physical values.

13. The method of claim 12, wherein step e) is directly followed by an by an amplitude test (28b) defined as a yes/no test whether the measurement data series indicates an amplitude of the excitation force conforming to a given range of amplitudes, wherein in the negative case of the amplitude test (28b) the program loops back to the measuring procedure (31), and wherein in the affirmative case of the amplitude test (28b), the program proceeds to step f).

14. The method of claim 12, further comprising a reset phase that follows the measuring phase and comprises:

g) a resetting step (33), wherein the direct current is reset to the stored DC value, the alternating current is reset to the stored AC value, and a re-test measurement series is performed with the reset values and with the test frequency $f_{test}$ of the alternating current, wherein in said re-test measurement series a re-test data series is determined for one of the deformation and the excitation force;

h) a decision step (26b), wherein a parameter value is assigned to the decision parameter based on said re-test measurement series and a yes/no test is made as to whether the parameter value indicates an insufficient amount of pre-tensioning force;

i) with a negative outcome of step h), proceeding to a DC-reducing step (34) based on an assumption that the pre-tensioning force is too high, performing another re-test measurement series with the reduced DC-value, and then looping back to step h;

j) with a positive outcome of step h), proceeding to the DC-adjusting step (27) and subsequent to step (27) continuing with step c) of the test phase.

15. An apparatus for performing a dynamic mechanical analysis on a test specimen, comprising a controller device for controlling the analysis, an excitation device operable to apply to the test specimen an excitation force comprised of a static pre-tensioning force component and a time-variable force component, a holder device for coupling the test specimen to the excitation device, and at least one displacement sensor operable to perform deformation measurements on the test specimen, wherein while said excitation force is being applied, the controller device determines at least one decision parameter, said decision parameter being indicative of a degree of slack in said coupling of the test specimen, wherein the controller compares said decision parameter to at least one given reference value and wherein said comparison provides an indication of whether or not the test specimen is coupled to the excitation device in a completely slack-free state, so that physical values derived from said deformation measurements will not be subject to errors caused by an insufficient amount of said pre-tensioning force component.

16. The apparatus of claim 15, wherein the controller device provides a representation of at least one of the deformation and an effective deformation-causing excitation force at least during limited time segments as a series of data assigned to sequential points in time, wherein the controller performs a test phase in which said series of data is compared to a reference profile, said reference profile being representative of said completely slack-free state, and wherein said decision parameter is defined so that it allows a quantitative comparison of said series of data to said reference profile.

17. The apparatus of claim 15, wherein the controller device determines a DC value of a direct current that produces the pre-tensioning force component required for said slack-free state and an AC value of an alternating current that produces the time-variable force component, and where the controller device determines said DC value and AC value in such a manner that said physical values will not be subject to said errors.

18. The apparatus of claim 17, wherein the controller performs a measurement phase to determine said physical values, and wherein after said measurement phase the controller lowers said DC value to such an extent that the DC value has to be raised and redetermined in such a manner that said physical values will not be subject to said errors in a next-following measurement phase.

* * * * *